(12) United States Patent
Allison et al.

(10) Patent No.: US 7,687,528 B2
(45) Date of Patent: *Mar. 30, 2010

(54) PHARMACEUTICAL COMPOSITIONS OF AN $AT_1$-RECEPTOR ANTAGONIST AND AN INSULIN SECRETION ENHANCER

(75) Inventors: Malcolm Allison, Basel (CH); Marjorie R Gatlin, Maplewood, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/508,353

(22) Filed: Aug. 23, 2006

(65) Prior Publication Data

US 2006/0281790 A1  Dec. 14, 2006

Related U.S. Application Data

(63) Continuation of application No. 11/295,928, filed on Dec. 7, 2005, now abandoned, which is a continuation of application No. 10/362,340, filed as application No. PCT/EP01/09587 on Aug. 20, 2001, now abandoned.

(60) Provisional application No. 60/327,553, filed on Aug. 22, 2000.

(51) Int. Cl.
*A61K 31/41* (2006.01)
(52) U.S. Cl. ..................................................... 514/381
(58) Field of Classification Search ............ 514/264.1, 514/381, 394, 563, 635
See application file for complete search history.

(56) References Cited

U.S. PATENT DOCUMENTS

| | | | |
|---|---|---|---|
| 5,298,497 A | 3/1994 | Tschollar et al. ............... | 514/91 |
| 5,616,599 A | 4/1997 | Yanagisawa et al. ......... | 514/381 |
| 5,663,186 A | 9/1997 | Nelson et al. ................ | 514/381 |
| 5,663,187 A | 9/1997 | Nelson et al. ................ | 514/381 |
| 5,952,356 A | 9/1999 | Ikeda et al. .................. | 514/340 |
| 6,251,926 B1 | 6/2001 | Momose et al. ............. | 514/364 |
| 6,559,188 B1 | 5/2003 | Gatlin et al. ................. | 514/641 |
| 6,878,749 B2 | 4/2005 | Gatlin et al. ................. | 514/641 |
| 2002/0037829 A1 | 3/2002 | Aronson et al. | |
| 2002/0037928 A1 | 3/2002 | Jaen et al. .................... | 514/616 |
| 2004/0087645 A1 | 5/2004 | Scholkens et al. ........... | 514/423 |

FOREIGN PATENT DOCUMENTS

| | | | |
|---|---|---|---|
| WO | WO 98/27974 | | 7/1998 |
| WO | WO 00/34241 | * | 6/2000 |
| WO | WO 00/45818 A | | 8/2000 |
| WO | WO 01/21602 A | | 3/2001 |

OTHER PUBLICATIONS

Giuiani et al., Mayo Clinic Practice of cardiology, third edition, by Mosby Publishing, pp. 1116-1121 (1996).
Handbook of Pharmaceutical Excipients, published by American Pharmaceutical Association (EC), in 1986, pp. 53-55 and 304-308.

* cited by examiner

*Primary Examiner*—Raymond J Henley, III
(74) *Attorney, Agent, or Firm*—Joseph T. Majka; Gregory D. Ferraro

(57) ABSTRACT

The present invention relates to a combination, especially a pharmaceutical composition, comprising as active ingredients
(i) an $AT_1$-receptor antagonist or a pharmaceutically acceptable salt thereof;
(ii) (a) an insulin secretion enhancer or a pharmaceutically acceptable salt thereof or (b) an insulin sensitizer or a pharmaceutically acceptable salt thereof; and,
in case of a pharmaceutical composition, a pharmaceutically acceptable carrier.

2 Claims, No Drawings

PHARMACEUTICAL COMPOSITIONS OF AN AT₁-RECEPTOR ANTAGONIST AND AN INSULIN SECRETION ENHANCER

This application is a continuation application of prior application Ser. No. 11/295,928, filed Dec. 7, 2005, now abandoned, which is a continuation of application Ser. No. 10/362,340, now abandoned, filed Jun. 16, 2003, which is a national stage of PCT/EP01/09587, filed Aug. 20, 2001 which claims benefit of Provisional Application No. 60/327,553, filed Aug. 22, 2000.

The present invention relates to a combination, especially a pharmaceutical composition, comprising as active ingredients (i) an $AT_1$-receptor antagonist or a pharmaceutically acceptable salt thereof;

(ii) (a) an insulin secretion enhancer or a pharmaceutically acceptable salt thereof or (b) an insulin sensitizer or a pharmaceutically acceptable salt thereof; and, in case of a pharmaceutical composition, a pharmaceutically acceptable carrier.

$AT_1$-receptor antagonists (also called angiotensin II receptor antagonists or blockers) are understood to be those active ingredients that bind to the $AT_1$-receptor subtype of angiotensin II receptor but do not result in activation of the receptor. As a consequence of the blockade of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds that are selected from the group consisting of valsartan (cf. EP 443983), losartan (cf. EP 253310), candesartan (cf. EP 459136), eprosartan (cf. EP403159), irbesartan (cf. EP 454511), olmesartan (cf. U.S. Pat. No. 5,616,599), tasosartan (cf. EP 539086), and telmisartan (cf. EP 502314), or, in each case, a pharmaceutically acceptable salt thereof.

Preferred $AT_1$-receptor antagonist are those agents that have been marketed, most preferred is valsartan or a pharmaceutically acceptable salt thereof.

Insulin secretion enhancers are active ingredients that have the property to promote the secretion of insulin from pancreatic β-cells. Examples of insulin secretion enhancers are sulfonylureas (SU), especially those which promote the secretion of insulin from pancreatic β-cells by transmitting signals of insulin secretion via SU receptors in the cell membrane, Including (but are not limited to) tolbutamide; chlorpropamide; tolazamide; acetohexamide; 4-chloro-N-[(1-pyrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or a pharmaceutically acceptable salt thereof.

Insulin secretion enhancers furthermore include short-acting insulin secretion enhancers, such as the new phenylalanine derivative nateglinide [N-(trans-4-isopropylcyclohexyl-carbonyl)-D-phenylalanine] (cf. EP 196222 and EP 526171) of the formula

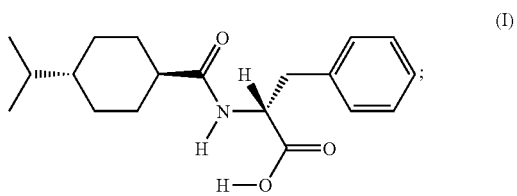

repaglinide [(S)-2-ethoxy-4-{2-[[3-methyl-1-[2-(1-piperidinyl)phenyl]butyl]amino]-2-oxoethyl}benzoic acid—cf. EP 589874]; calcium (2S)-2-benzyl-3-(cis-hexahydro-2-isoindolinlycarbonyl)-propionate dihydrate (mitiglinide—cf. EP 507534); furthermore representatives of the new generation of SUs such as glimepiride (cf. EP 31058); and in free or pharmaceutically acceptable salt form.

Insulin secretion enhancers likewise include the long-acting insulin secretion enhancer DPP-IV inhibitors, GLP1 and GLP1 agonists.

DPP-IV is responsible for Inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, for example, pyrrolidine, 1-[(3-hydroxy-1-adamantyl)amino]acetyl-2-cyano-, (S), respectively.

GLP-1 is a insulinotropic proteine which was described, e.g., by W. E. Schmidt et al. in Diabetologia 28, 1985, 704-707 and in U.S. Pat. No. 5,705,483.

The term "GLP-1 agonists" used herein means variants and analogs of GLP-1 (7-36)$NH_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. The term "GLP-1 agonists" comprises especially compounds like GLP-1 (7-37), in which compound the carboxy-terminal amide functionality of $Arg^{36}$ is displaced with Gly at the $37^{th}$ position of the GLP-1 (7-36) $NH_2$ molecule and variants and analogs thereof including $GLN^9$-GLP-1 (7-37), D-$GLN^9$-GLP-1 (7-37), acetyl $LYS^9$-GLP-1 (7-37), $LYS^{18}$-GLP-1 (7-37) and, in particular, GLP-1(7-37)OH, $VAL^8$-GLP-1 (7-37), $GLY^8$-GLP-1 (7-37), $THR^8$-GLP-1 (7-37) and 4-imidazopropionyl-GLP-1. Special preference is also given to the GLP agonist analog exendin-4, described by Greig et al in Diabetologia 1999, 42, 45-50.

A preferred insulin secretion enhancer is repaglinide, most preferred is nateglinide.

The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 (being directed to the H-form crystal modification) as well as the corresponding references to the B-form crystal modification.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The term "short-acting insulin secretion enhancer" comprises corresponding agents with a maximum secretion of insulin that is attained within one hour, preferably within 30 minutes, after the administration of the agent, most preferably within 20 minutes having a biological half-life, T ½, of less than two hours, preferably, 1.5 hours. The term long-acting insulin secretion enhancer" comprises corresponding agents with a maximum secretion of insulin that is attained more than one hour after administration of the agent.

A preferred insulin sensitizer is metformin or a pharmaceutically acceptable salt thereof such as the mono-hydrochloride.

Especially preferred is a combination of valsartan or a pharmaceutically acceptable salt thereof and nateglinide or a pharmaceutically acceptable salt thereof.

The corresponding active ingredients or a pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

The pharmaceutical activities as effected by administration of representatives of the class of $AT_1$-receptor antagonists or insulin secretion enhancers, respectively, or of the combination of active agents used according to the present invention can be demonstrated e.g. by using corresponding pharmacological models known In the pertinent art. The person skilled In the pertinent art is fully enabled to select a relevant animal test model to prove the hereinbefore and hereinafter indicated therapeutic indications and beneficial effects.

To evaluate the antihypertensive activity of the combination according to the invention, for example, the methodology as described by Lovenberg W: Animal models for hypertension research. Prog. Clin. Biol. Res. 1987, 229, 225-240 may be applied. For the evaluation that the combination according to the present invention may be used for the treatment of congestive heart failure, for example, the methods as disclosed by Smith H J, Nuttall A: Experimental models of heart failure. Cardiovasc Res 1985, 19, 181-186 may be applied. Molecular approaches such as transgenic methods are also described, for example by Luft et al.: Hypertension-induced end-organ damage. "A new transgemic approach for an old problem." Hypertension 1999, 33, 212-218.

The insulin secretion enhancing properties of the combination according to the present invention may be determined by following the methodology as disclosed, for example, in the publication of T.Ikenoue et al. Biol.Pharm.Bull. 29(4), 354-359 (1997).

The corresponding subject matter of these four references is herewith incorporated by reference in this specification.

Accordingly, the combination according to the present invention may be used,. e.g., for the prevention, delay of progression or treatment of diseases and disorders that may be inhibited by the inhibition of AT, receptor, that may be inhibited by the enhancement of insulin secretion and that may be inhibited by insulin sensitization. Especially, the combination according to the present invention may be used, e.g., for the prevention, delay of progression or treatment of diseases and disorders selected from the group consisting of hypertension, congestive heart failure, diabetes, especially type 2 diabetes mellitus, diabetic retinopathy, macular degeneration, diabetic nephropathy, glomerulosclerosis, chronic renal failure, diabetic neuropathy, syndrome X, premenstrual syndrome, coronary heart disease, angina pectoris, myocardial infarction, stroke, vascular restenosis, hyperglycemia, hyperinsulinaemia, hyperlipidaemia, hypertryglyceridemia, insulin resistance, impaired glucose metabolism, conditions of impaired glucose tolerance (IGT), conditions of impaired fasting plasma glucose, obesity, diabetic retinopathy, macular degeneration, cataracts, diabetic nephropathy, glomerulosclerosis, diabetic neuropathy, erectile dysfunction, premenstrual syndrome, skin and connective tissue disorders, foot ulcerations and ulcerative colitis, endothelial dysfunction and impaired vascular compliance. Preferably, said combination may be used for the treatment of hypertension, especially ISH, congestive heart failure, endothelial dysfunction, impaired vascular compliance, IGT and type II diabetes mellitus.

A "disease or condition which may be inhibited by the Inhibition of $AT_1$ receptor" as defined in this application comprises, but is not limited to hypertension, congestive heart failure, diabetes, especially type 2 diabetes mellitus, diabetic retinopathy, macular degeneration, diabetic nephropathy, glomerulosclerosis, chronic renal failure, diabetic neuropathy, syndrome X, premenstrual syndrome, coronary heart disease, angina pectoris, myocardial infarction, stroke, vascular restenosis, endothelial dysfunction and the like. A "disease or condition which may be inhibited by the enhancement of insulin secretion" as defined In this application comprises, but Is not limited to hyperglycemia, hyperinsulinaemia, hyperlipidaemia, hypertryglyceridemia, insulin resistance, impaired glucose metabolism, conditions of impaired glucose tolerance (IGT), conditions of impaired fasting plasma glucose, obesity, diabetic retinopathy, macular degeneration, cataracts, diabetic nephropathy, glomerulosclerosis, diabetic neuropathy, erectile dysfunction, premenstrual syndrome, coronary heart disease, hypertension, angina pectoris, myocardial infarction, stroke, vascular restenosis, skin and connective tissue disorders, foot ulcerations and ulcerative colitis, endothelial dysfunction and impaired vascular compliance.

A "disease or condition that may be inhibited by insulin sensitization" as defined in this application comprises, but is not limited to hyperglycemia, hyperinsulinaemia, hyperlipidaemia, hypertryglyceridemia, insulin resistance, impaired glucose metabolism, conditions of impaired glucose tolerance (IGT), conditions of Impaired fasting plasma glucose, obesity, diabetic retinopathy, macular degeneration, cataracts, diabetic nephropathy, glomerulosclerosis, diabetic neuropathy, erectile dysfunction, premenstrual syndrome, coronary heart disease, hypertension, angina pectoris, myocardial infarction, stroke, vascular restenosis, skin and connective tissue disorders, foot ulcerations and ulcerative colitis, endothelial dysfunction and impaired vascular compliance.

Hypertension, in connection with a "disease or condition which may be inhibited by the inhibition of $AT_1$, receptor", a "disease or condition which may be Inhibited by the enhancement of insulin secretion", a "disease or condition that may be inhibited by insulin sensitization" includes and is not limited to mild, moderate and severe hypertension as defined in Journal of Hypertension 1999, 17:151-183, especially on page 162. Especially preferred is "isolated systolic hypertension" (ISH).

Preferably, the jointly therapeutically effective amounts of the active agents according to the combination of the present invention can be administered simultaneously or sequentially in any order, e.g. separately or in a fixed combination.

Under certain circumstances, drugs with different mechanisms of action may be combined. However, just considering any combination of drugs having different modes of action but acting in the similar field does not necessarily lead to combinations with advantageous effects.

All the more surprising is the experimental finding that the combined administration of an $AT_1$ receptor antagonist and insulin secretion enhancer and/or an insulin sensitizer, or, in each case, a pharmaceutically acceptable form thereof, results not only in a beneficial, especially a potentiating or a synergistic, therapeutic effect. Independent thereof, additional benefits resulting from combined treatment can be achieved such as a surprising prolongation of efficacy, a broader variety of therapeutic treatment and surprising beneficial effects on diseases and conditions associated with diabetes, e.g. less gain of weight. An additional and preferred aspect of the present invention is the prevention, delay of progression or treatment of the condition of isolated systolic hypertension and impaired vascular compliance which means decreased vascular elasticity.

The term "potentiation" shall mean an increase of a corresponding pharmacological activity or therapeutical effect, respectively. Potentiation of one component of the combination according to the present invention by co-administration of an other component according to the present invention means that an effect is being achieved that is greater than that achieved with one component alone.

The term "synergistic" shall mean that the drugs, when taken together, produce a total joint effect that is greater than the sum of the effects of each drug when taken alone.

ISH is the most common form of hypertension in people over 50 years. It is defined as elevated systolic blood pressure (above 140 mm Hg) in conjunction with normal diastolic blood pressure (below 90 mm Hg). Elevated systolic blood pressure is an Independent risk factor for cardiovascular diseases and may lead e.g. to myocardial hypertrophy and heart failure. ISH is furthermore characterized by an increased pulse pressure, defined as the difference between systolic and diastolic blood pressures. Elevated pulse pressure is being recognized as the type of hypertension the least likely to be well controlled. A reduction of elevated systolic blood pressure and correspondingly of pulse pressure is associated with a significant risk reduction in cardiovascular death. It has surprisingly been found that the combination of an $AT_1$ receptor antagonist and an insulin secretion enhancer or an insulin sensitizer leads to a decrease of ISH and pulse rate, both in hypertensive patients having type 2 diabetes mellitus and in hypertensive patient that do not have type 2 diabetes mellitus.

Furthermore, it has been found that the chronic co-administration of either an insulin sensitizer or an insulin secretion enhancer imparts the beneficial effect on blood vessel morphology and function and results in a decrease of vascular stiffness and correspondingly in a maintenance and in an improvement of vascular compliance.

Accordingly, it has been found that the addition of an insulin sensitizer and/or an insulin secretion enhancer to that of an $AT_1$ receptor antagonist would potentiate the effect on systolic blood pressure and further improve vascular stiffness/compliance. Conversely, the proven antihypertensive effects of an $AT_1$ receptor antagonist on systolic and diastolic blood pressure may be potentiated by the addition of an insulin sensitizer and/or an insulin secretion enhancer. The benefit of these combinations may also extend to an additional or potentiated effect on endothelial function, and improve vascular function and structure in various organs/tissues including the kidney, heart, eye and brain. Through the reduction in glucose levels, an anti-thrombotic and anti-atherosclerotic effect can also be demonstrated. Reduction of glucose would prevent or minimize the glycosylation of any structural or functional protein within the cardio-renal system. This effect proves to be highly beneficial by evoking an additive or synergistic effect on vascular function/structure when administered with an $AT_1$ receptor antagonist which alone improves cardiovascular function and structure through a distinct mechanism.

Further benefits are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

For example, it has turned out that the combination according to the present invention provides benefit especially in the treatment of modest hypertension or isolated systolic hypertension that is beneficial to all diabetic patients regardless of their hypertensive status, e.g. reducing the risk of negative cardiovascular events by two different modes of action.

The $AT_1$ receptor antagonists, especially valsartan, have proven to be also useful in the treatment of type 2 diabetes mellitus beyond the reduction of blood pressure in for example improving microalbuminuria. At sub-therapeutic doses, with respect to the treatment of hypertension, the combination according to the invention may be merely used for the treatment of diabetes, especially type 2 diabetes mellitus. In view of the reduced dose of the $AT_1$ receptor antagonist, there is a considerable safety profile of the combination making it suitable for first line therapy.

The present invention relates to the use of a combination comprising as active ingredients
  (i) an $AT_1$-receptor antagonist or a pharmaceutically acceptable salt thereof;
  (ii) (a) an insulin secretion enhancer or a pharmaceutically acceptable salt thereof or (b) an insulin sensitizer or a pharmaceutically acceptable salt thereof;

for the manufacture of a medicament for the prevention, delay of progression or treatment of a disease and disorder which may be inhibited by the inhibition of $AT_1$ receptor and by the enhancement of insulin secretion, for example, for the prevention, delay of progression or treatment of hypertension, especially modest hypertension, ISH, congestive heart failure, endothelial dysfunction, impaired vascular compliance, IGT and type II diabetes mellitus.

The present invention also relates to a method for the prevention, delay of progression or treatment of a disease and disorder which may be inhibited by the inhibition of $AT_1$ receptor and/or by the enhancement of insulin secretion comprising administering to a warm-blooded animal, including man, in need thereof jointly therapeutically effective amounts of
(i) an $AT_1$-receptor antagonist or a pharmaceutically acceptable salt thereof;
(ii) (a) an insulin secretion enhancer or a pharmaceutically acceptable salt thereof or (b) an insulin sensitizer or a pharmaceutically acceptable salt thereof.

The pharmaceutical composition according to the present invention as described hereinbefore and hereinafter may be used for simultaneous use or sequential use in any order, for separate use or as a fixed combination.

The pharmaceutical composition according to the present invention comprises a "kit of parts" in the sense that the components can be dosed independently or by use of different fixed combinations with distinguished amounts of the components at different time points. The parts of the "kit of parts" can then e.g. be administered simultaneously or chronologically staggered, that is at different time points and with equal or different time Intervals for any part of the "kit of parts". Preferably, the time intervals are chosen such that the effect on the treated disease or condition in the combined use of the parts is larger than the effect that would be obtained by use of only any one of the components. Preferably, there is at least one beneficial effect, e.g. a mutual enhancing of the effect of
(i) an $AT_1$-receptor antagonist or a pharmaceutically acceptable salt thereof;
(ii) (a) an insulin secretion enhancer or a pharmaceutically acceptable salt thereof or (b) an insulin sensitizer or a pharmaceutically acceptable salt thereof;

in particular a potentiation or a synergism, e.g. a more than additive effect, additional advantageous effects, less side effects, a combined therapeutic effect in a non-effective dosage of one or each of the components, especially a potentiation or a strong synergism.

The invention furthermore relates to a commercial package comprising the combination according to the present invention together with instructions for simultaneous, separate or sequential use.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubilizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those which are commerically available.

Normally, in the case of oral administration, an approximate daily dose of from about 1 mg to about 360 mg is to be estimated e.g. for a patient of approximately 75 kg in weight.

The dosage of the active compound can depend on a variety of factors, such as mode of administration, homeothermic species, age and/or individual condition.

Valsartan, as a representative of the class of $AT_1$-receptor antagonists, will be supplied in the form of suitable dosage unit form, for example, a capsule or tablet, and comprising a therapeutically effective amount, e.g. from about 20 to about 320 mg, of valsartan which may be applied to patients. The application of the active Ingredient may occur up to three times a day, starting e.g. with a daily dose of 20 mg or 40 mg of valsartan, increasing via 80 mg daily and further to 160 mg daily up to 320 mg daily. Preferably, valsartan is applied twice a day with a dose of 80 mg or 160 mg, respectively, each. In a low-does formulation, valsartan with a dose of 20 mg or 40 mg may be used. Corresponding doses may be taken, for example, in the morning, at mid-day or in the evening. Preferred is b.i.d. administration.

The insulin secretion enhancer nateglinide (I) is preferably administered to the warm-blooded animal in a dosage in the range of about 5 to 1200, more preferably 25 to 800, mg/day, when the warm-blooded animal is a human of about 70 kg body weight. Preferred dosages contain 30 mg, 60 mg, 120 mg or 180 mg of nateglinde to be administered preferably before the main meals. In a low dose combination, the dosage of nategilnide to be administered preferably is 30 mg, 40 mg or furthermore 60 mg. Depending on the number of main meals the dose regimen are two times a day (BID) or three times a day (TID) or four times a day (QID).

The insulin secretion enhancer repaglinde is preferably administered in a dosage range of about 0.01 mg to about 8 mg, more preferred from about 0.5 to about 6 mg.

The insulin sensitizer metformin is preferably administered in a dosage range of about 100 mg to about 1200 mg per dose unit, especially 500 mg, 850 mg or 1000 mg. In a low dose combination, metformin is preferably administered in a dosage of 125 mg, 250 mg or 500 mg.

FORMULATION EXAMPLE 1

Film-Coated Tablets:

| Components | Compostion Per Unit (mg) | Standards |
|---|---|---|
| Granulation | | |
| Valsartan [=active ingredient] | 80.00 | |
| Microcrystalline cellulose/ Avicel PH 102 | 54.00 | NF, Ph. Eur |
| Crospovidone | 20.00 | NF, Ph. Eur |
| Colloidal anhydrous silica/ colloidal silicon dioxide/Aerosil 200 | 0.75 | Ph. Eur/ NF |
| Magnesium stearate | 2.5 | NF, Ph. Eur |
| Blending | | |
| Colloidal anhydrous silica/ colloidal silicon dioxide/Aerosil 200 | 0.75 | Ph. Eur/ NF |
| Magnesium stearate | 2.00 | NF, Ph. Eur |
| Coating | | |
| Purified water*⁾ | — | |
| DIOLACK pale red 00F34899 | 7.00 | |
| Total tablet mass | 167.00 | |

*⁾Removed during processing.

The film-coated tablet is manufactured e.g. as follows:

A mixture of valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a scrennning mill. The resulting mixture is again premixed In a diffusion mixer, compacted In a roller compacter and then sieve through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tabletts are coated with a film by using Diolack pale red in a perforated pan.

FORMULATION EXAMPLE 2

Film-Coated Tablets:

| Components | Compostion Per Unit (mg) | Standards |
|---|---|---|
| Granulation | | |
| Valsartan [=active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ colloidal silicon dioxide/Aerosil 200 | 1.50 | Ph. Eur/ NF |
| Magnesium stearate | 5.00 | NF, Ph. Eur |
| Blending | | |
| Colloidal anhydrous silica/ colloidal silicon dioxide/Aerosil 200 | 1.50 | Ph. Eur/ NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

FORMULATION EXAMPLE 3

Film-Coated Tablets:

| Components | Compostion Per Unit (mg) | Standards |
|---|---|---|
| Core: Internal phase | | |
| Valsartan [=active ingredient] | 40.00 | |
| Silica, colloidal anhydrous (Colloidal silicon dioxide) [=Glidant] | 1.00 | Ph. Eur, USP/NF |
| Magnesium stearate [=Lubricant] | 2.00 | USP/NF |
| Crospovidone [Disintegrant] | 20.00 | Ph. Eur |
| Microcrystalline cellulose [=Binding agent] | 124.00 | USP/NF |
| External phase | | |
| Silica, colloidal anhydrous, (Colloidal silicon dioxide) [=Glidant] | 1.00 | Ph. Eur, USP/NF |
| Magnesium stearate [Lubricant] | 2.00 | USP/NF |
| Film coating | | |
| Opadry ® brown OOF 16711*⁾ | 9.40 | |
| Purified Water**⁾ | — | |
| Total tablet mass | 199.44 | |

*⁾The composition of the Opadry ® brown OOF16711 coloring agent is tabulated below.
**⁾Removed during processing Opadry® Composition:

| Ingredient | Approximate % Composition |
|---|---|
| Iron oxide, black (C.I. No. 77499, E 172) | 0.50 |
| Iron oxide, brown (C.I. No. 77499, E 172) | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

FORMULATION EXAMPLE 4

Capsules:

| Components | Compostion Per Unit (mg) |
|---|---|
| Valsartan [=active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 209.50 |

The tablet is manufactured e.g. as follows:

Granulation/Drying

Valsartan and microcrystallin cellulose are spray-granulated in a fluidised bed granulator with a granulating solution consisting of povidone and sodium lauryl sulphate dissolved in purified water. The granulate obtained is dried in a fluidiesd bed dryer.

Milling/Blending

The dried granulate is milled together with crospovidone and magnesium stearate. The mass is then blended in a conical srew type mixer for approximately 10 minutes.

Encapsulation

Teh empty hard gelatin capsules are filled with the blended bulk granules under controlled temperature and humidity conditions. The filed capsules are dedustee, visually inspected, weightchecked and quarantied until by Quality assurance department.

FORMULATION EXAMPLE 5

Capsules:

| Components | Composition Per Unit (mg) |
|---|---|
| Valsartan [=active ingredient] | 160.00 |
| Microcrystalline cellulose | 50.20 |
| Crospovidone | 26.00 |
| Povidone | 25.00 |
| Magnesium stearate | 2.60 |
| Sodium lauryl sulphate | 1.20 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 342.00 |

The formulation is manufactured e.g. as described in Formulation Example 4.

FORMULATION EXAMPLE 6

Hard Gelatine Capsule:

| Components | Composition Per Unit (mg) |
|---|---|
| Valsartan [=active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

EXAMPLES 7 to 11

| Components | 7 Composition per unit (mg) | 8 Composition per unit (mg) | 9 Composition per unit (mg) | 10 Composition per unit (mg) | 11 Composition per unit (mg) |
|---|---|---|---|---|---|
| Granulation | | | | | |
| Valsartan Drug Substance (DS) | 80.000 | 160.000 | 40.000 | 320.000 | 320.000 |
| Microcrystalline Cellulose (NF, *Ph. Eur.*)/ Avicel PH 102 | 54.000 | 108.000 | 27.000 | 216.000 | 216.000 |
| Crospovidone (NF, *Ph. Eur.*) | 15.000 | 30.000 | 7.500 | 80.000 | 60.000 |
| Colloidal Anhydrous Silica (*Ph. Eur.*)/Colloidal Silicon Dioxide (NF)/Aerosil 200 | 1.500 | 3.000 | 0.750 | 3.000 | 6.000 |
| Magnesium Stearate (NF, *Ph. Eur.*) | 3.000 | 6.000 | 1.500 | 10.000 | 12.000 |
| Blending | | | | | |
| Colloidal Anhydrous Silica (*Ph. Eur.*)/Colloidal Silicon Dioxide (NF)/Aerosil 200 | — | — | — | 3.000 | — |
| Magnesium Stearate, NF, *Ph. Eur.* | 1.500 | 3.000 | 0.750 | 8.000 | 6.000 |
| Core Weight/mg | 155.000 | 310.000 | 77.500 | 640.000 | 620.000 |
| Coating | — | — | 3.800 | 15.000 | 16.000 |

EXAMPLE 12

108,000 tablets, each which contain 120 mg of nateglinide are prepared as follows:

| Composition: | nateglinide | 12.960 kg |
|---|---|---|
| | lactose, NF | 30.564 kg |
| | microcrystalline cellulose, NF | 15.336 kg |
| | povidone, USP | 2.592 kg |
| | croscarmellose sodium, NF | 3.974 kg |
| | colloidal silicon dioxide, NF | 1.382 kg |
| | magnesium stearate, NF | 1.231 kg |
| | coating: opadry yellow | 1.944 kg |
| | purified water, USP* | Q.S. |

*removed during process

Preparation process: The microcrystalline cellulose, povidone, part of the croscarmellose sodium, nateglinide and lactose are mixed in a high shear mixer and afterwards granulated using purified water. Alternatively, the microcrystalline cellulose, povidone, a portion of the croscarmellose sodium, nateglinide and lactose are granulated in a collette gral granulator with the addition of purified water. The wet granules are dried in a fluid bed dryer and passed through a screen. The colloidal silicon dioxide and the rest of the croscarmellose sodium are mixed, passed through a screen and blended with the dried granules in a V-blender. The magnesium stearate Is passed through a screen, blended with the blend from the V-blender and afterwards the total mixture is compressed to tablets. The opadry yellow is suspended in purified water and the tablets are coated with the coating suspension.

EXAMPLES 13-15

| Component | 60 mg | 120 mg | 180 mg |
|---|---|---|---|
| Starlix DS (H-form crystal modification) | 60 | 120 | 180 |
| Lactose Monohydrate | 141.5 | 283 | 214 |
| MicrocrystallineCellulose | 71 | 142 | 107 |
| Povidone K30 | 12 | 24 | 23 |
| Croscarmellose Sodium | 12 | 24 | 34 |
| Sub-Total (Granulation) | 296.5 | 593 | 558 |
| Croscarmellose Sodium | 6.4 | 12.8 | 24.5 |
| Colloidal Silicone Dioxide | 6.4 | 12.8 | 12.3 |
| Magnesium Stearate | 5.7 | 11.4 | 15.2 |
| Sub-Total (Core) | (315) | (630) | (610) |
| Opadry | 9 | 18 | 18 |
| Total | 324 | 648 | 628 |

What is claimed is:

1. A method for the inhibition of the onset of, delay of progression or treatment of diabetes and/or complications therefrom comprising administering a therapeutically effective amount of a suitable dosage form consisting essentially of the AT1-receptor antagonist, valsartan.

2. The method of claim 1 wherein the diabetes is type 2 diabetes mellitus.

* * * * *